United States Patent
Lehtikoski et al.

(10) Patent No.: US 7,508,509 B2
(45) Date of Patent: Mar. 24, 2009

(54) MEASUREMENT OF AN OBJECT FROM AN IMAGE CONSISTING OF A PIXEL MATRIX

(75) Inventors: Pekka Lehtikoski, Alpharetta, GA (US); Antti Salopuro, Varkaus (FI)

(73) Assignee: Metso Automation Oy, Helsinki (FI)

( * ) Notice: Subject to any disclaimer, the term of this patent is extended or adjusted under 35 U.S.C. 154(b) by 318 days.

(21) Appl. No.: 11/118,579

(22) Filed: Apr. 29, 2005

(65) Prior Publication Data
US 2005/0248762 A1 Nov. 10, 2005

Related U.S. Application Data

(60) Provisional application No. 60/567,963, filed on May 4, 2004.

(51) Int. Cl.
*G01N 21/00* (2006.01)
(52) U.S. Cl. ................................ 356/338; 356/343
(58) Field of Classification Search ................ 356/338, 356/343
See application file for complete search history.

(56) References Cited

U.S. PATENT DOCUMENTS

| | | | | |
|---|---|---|---|---|
| 3,830,969 A | * | 8/1974 | Hofstein | 348/127 |
| 5,159,642 A | * | 10/1992 | Kosaka | 382/134 |
| 5,311,290 A | * | 5/1994 | Olson et al. | 356/634 |
| 5,570,181 A | * | 10/1996 | Yasuo et al. | 356/336 |
| 5,786,894 A | * | 7/1998 | Shields et al. | 356/338 |
| 6,311,550 B1 | * | 11/2001 | Lehmikangas et al. | 73/61.71 |
| 6,407,819 B1 | * | 6/2002 | Kuratle | 356/634 |
| 6,703,618 B2 | * | 3/2004 | Karki et al. | 250/373 |
| 6,960,756 B1 | * | 11/2005 | Penumadu et al. | 250/222.2 |
| 7,019,834 B2 | * | 3/2006 | Sebok et al. | 356/335 |

FOREIGN PATENT DOCUMENTS

| | | |
|---|---|---|
| JP | 10090159 | 4/1998 |
| JP | 11337470 | 12/1999 |

OTHER PUBLICATIONS

Majid R. Feddah and Neal M. Davies; *Alternative Methods of Particle Size Analysis of Metered Dose Inhaler Aerosols*; J. Med Sci.; Jan.-Mar. 2004; pp. 63-69.

Carolina Wählby, Joakim Linblad, Mikael Vondrus, Ewert Bengtsson and Lennart Björksten; *Algorithms for cytoplasm segmentation of fluorescence labeled cells*; Analytical Cellular Pathology; 2002; pp. 101-111, p. 105, chapter 2.3; IOS Press.

Search Report for International Appl. No. PCT/FI2005/050143 mailed Jul. 25, 2005.

* cited by examiner

*Primary Examiner*—Roy M Punnoose
(74) *Attorney, Agent, or Firm*—Alston & Bird LLP (57) ABSTRACT

An image of an object is formed on a matrix detector consisting of pixels and a property dependent on at least one dimension is measured by means of a value related to the object and proportional to the intensity of the optical radiation detected by at least one pixel.

35 Claims, 3 Drawing Sheets

FIG. 1

| 0.1 | 0.1 | 0.5 | 0.9 | 0.6 | 0.1 | 0.1 |
|-----|-----|-----|-----|-----|-----|-----|
| 0.1 | 0.1 | 0.5 | 0.8 | 0.9 | 0.7 | 0.1 |
| 0.1 | 0.1 | 0.1 | 0.8 | 0.9 | 1.0 | 0.7 |
| 0.1 | 0.1 | 0.1 | 0.8 | 1.0 | 0.6 | 0.1 |
| 0.1 | 0.1 | 0.5 | 0.8 | 1.0 | 0.6 | 0.1 |
| 0.1 | 0.1 | 0.1 | 0.3 | 0.7 | 0.3 | 0.1 |
| 0.1 | 0.1 | 0.1 | 0.1 | 0.1 | 0.1 | 0.1 |

MEASUREMENT OF AN OBJECT FROM AN IMAGE CONSISTING OF A PIXEL MATRIX

CROSS-REFERENCE TO RELATED APPLICATIONS

This application claims the benefit of U.S. Provisional Application No. 60/567,963 filed May 4, 2004, which is incorporated herein in its entirety.

BACKGROUND OF THE INVENTION

1) Field of the Invention

The invention relates to measuring a physical object, such as fibers as used in pulp and paper processes, from an image consisting of a pixel matrix.

2) Description of Related Art

In the fiber processes employed in the paper industry, for example, the average length of fibers and the fiber length distribution are often highly relevant parameters. One way of measuring these variables is to image a low-density fiber suspension where fibers are dispersed into water functioning as the medium and try to determine a representative number of sample fibers from the fiber pulp by an automatic image processing device to find out the pulp characteristics. In addition to fibers, dimensions of other particles may also be determined.

The measurement is usually carried out in a narrow capillary tube or in a planar measurement cell, which spreads the sample pulp to be measured into a two-dimensional mat. In the capillary tube, the particles to be measured pass by the imaging camera one after another. In the planar measurement cell, a large number of particles to be measured are imaged simultaneously. Representativeness can be achieved by measuring a sufficiently large number of particles.

A problem associated with the above-mentioned solutions is that the accuracy of dimension measurement is determined in the automatic image processing device by the pixel size of the pixel matrix functioning as the detector. The particle dimension will be the multiple of the pixel diameter in the measurement direction. If, in that case, the diameter of the particle image on the detector is sufficient for covering only a few pixels, the measurement accuracy is low (the error may be tens of percents). The success of zooming also affects the accuracy, which will be poor when particles large in proportion to the pixel size are imaged. The fuzziness of the image may result from inadequate zooming or from the fact that an accurate image of the fiber inside the medium is unobtainable due to optical interference.

BRIEF SUMMARY OF THE INVENTION

The object of the invention is to provide an improved method, computer program and measurement device.

This is achieved by a method of measuring an object, where an image of the object is formed from a pixel matrix, the method comprising measuring at least one object dimension parallel with the image plane by means of a value related to the object and proportional to the intensity of the optical radiation detected by at least one pixel, the value of at least one of the above-mentioned pixels being between a predetermined upper limit value and lower limit value.

This is further achieved by a method of measuring particles, where at least one particle is dispersed into a medium in a measurement cell, the refractory index of the medium differing from the refractory index of the particle, the method comprising directing optical radiation at the measurement cell and forming an image of at least one particle in the measurement cell on a matrix detector consisting of pixels by means of the radiation exiting from the measurement cell, and the method comprising measuring a particle dimension parallel with the image plane by means of a value related to the particle and proportional to the intensity of the optical radiation detected by at least one pixel, the value of at least one of the above-mentioned pixels being between a predetermined upper limit value and lower limit value.

This is further achieved by a computer program for carrying out a computer process, which, when run, measures an object whose image is formed from a pixel matrix, the computer process comprising measuring at least one object dimension parallel with the image plane by means of a value related to the object and proportional to the intensity of the optical radiation detected by at least one pixel, the value of at least one of the above-mentioned pixels being between a predetermined upper limit value and lower limit value.

This is further achieved by a computer program for carrying out a computer process, which, when run, measures at least one particle, which is dispersed into a medium in a measurement cell, the refractory index of the medium differing from the refractory index of the particle, when optical radiation is directed at the measurement cell and an image is formed from at least one particle in the measurement cell on a matrix detector consisting of pixels by means of the radiation exiting from the measurement cell, the computer process comprising measuring a particle dimension parallel with the image plane by means of at least one value related to the particle and proportional to the intensity of the optical radiation detected by at least one pixel, the value of at least one of the above-mentioned pixels being between a predetermined upper limit value and lower limit value.

This is further achieved by a measurement device for measuring an object, the measurement device comprising a matrix detector, which consists of pixels and on which an image of the object is formed, and an automatic image processing unit, which is arranged to measure at least one object dimension parallel with the image plane by means of a value related to the object and proportional to the intensity of the optical radiation detected by at least one pixel, the value of at least one of the above-mentioned pixels being between a predetermined upper limit value and lower limit value.

This is further achieved by a measurement device for measuring a particle, the measurement device comprising a measurement cell, where at least one particle is dispersed into a medium whose refractory index differs from the refractory index of the particle, an optical radiation source for directing optical radiation at the measurement cell, a detector, which comprises a matrix consisting of detecting pixels and on which the optical radiation exiting from the measurement cell forms an image of at least one particle in the measurement cell, and an automatic image processing unit, which is arranged to measure at least one particle dimension parallel with the image plane by means of a value related to the particle and proportional to the intensity of the optical radiation detected by at least one pixel, the value of at least one of the above-mentioned pixels being between a predetermined upper limit value and lower limit value.

Preferred embodiments of the invention are described in the dependent claims.

The method and system according to the invention provide several advantages. The dimension to be measured can be measured with an accuracy greater than the pixel size. Also, measurement performed on fuzzy images will become more accurate.

BRIEF DESCRIPTION OF THE DRAWINGS

The invention will now be described in greater detail by means of preferred embodiments, with reference to the accompanying drawings, in which.

DETAILED DESCRIPTION OF THE INVENTION

Figure 1:
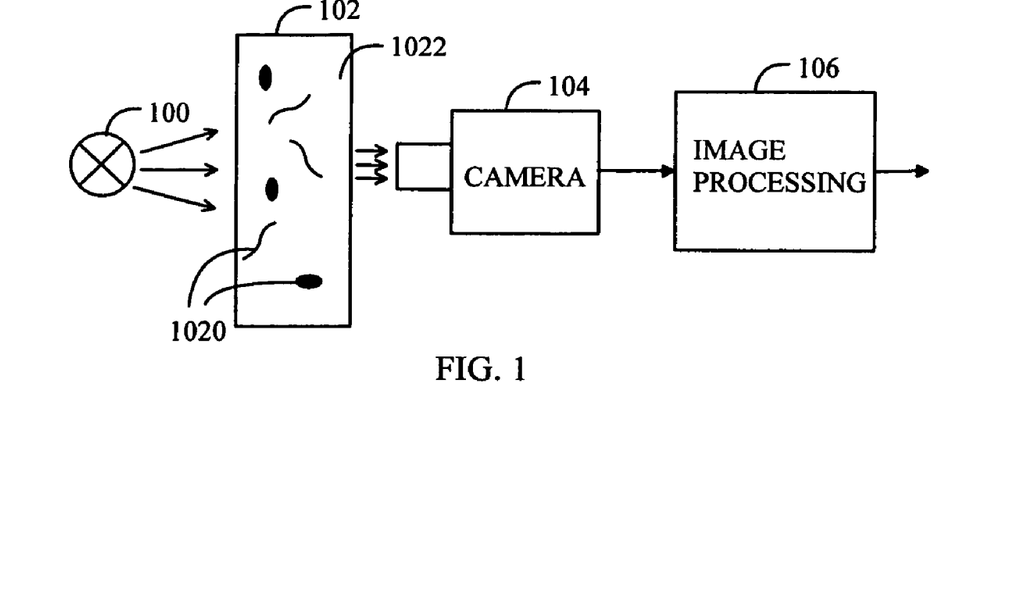
FIG. 1 illustrates a measurement arrangement.

The present solution is first examined by means of FIG. 1. Optical radiation is directed from an optical radiation source 100 at a measurement cell 102, which includes low-density suspension containing wood fibers, for example (the density range may be from 0.001% to 0.003% without being limited to this). In addition to wood fibers, the particles 1020 may be fine particles 1020 in a medium 1022. Instead of the fiber suspension, most different particles solid, liquid or gaseous substances may in a general case be dispersed into a gaseous medium. Furthermore, in a general case, particles of liquid and solid substances may be dispersed into a gaseous medium. The optical radiation source 100 may emit ultraviolet radiation, visible light or infrared radiation. The detector 104 may be a camera which is sensitive to optical radiation and comprises a detecting pixel matrix. The pixel matrix may be a semiconductor component, such as a CCD cell (Charge Coupled Device). As the optical radiation directed at the measurement cell 102 exits from the measurement cell 102, an image of the desired kind can be formed from the mixture of particles and medium inside the measurement cell 102 on the detector 104 by means of an optical component that forms an image, such as a lens. The optical radiation source 100 and the detector 104 may be on the opposite sides of the measurement cell 102, in which case the measurement cell 102 is transilluminated.

The image can also be formed by directing collimated optical radiation from the optical radiation source 100 at the measurement cell 102 from the opposite side of the detector 104 without the image-forming optical component, in which case the measurement cell 102 is transilluminated.

In the transillumination measurement, the goal may be to create a view where there is at least one dark particle on a light background. The detector may thus employ a collimating optical component, etc., in which case the detector has a small numerical opening. When a small numerical opening is used, only optical rays that travel without deviating in any direction reach the detecting pixel matrix. This happens to the optical radiation that travels in the measurement cell 102 through mere medium 1022. This appears as brightness or lightness in the image. If there is an interface that refracts or scatters radiation, such as an interface between a particle and a medium, on the path of optical radiation, the optical radiation does not reach the corresponding point on the detecting pixel matrix (at least not to the same extent as when optical radiation passes through mere medium). This appears as a black or dark area in the image. When a two-dimensional fiber suspension, for example, is imaged by scattering optics of this kind, each fiber on the path of optical radiation generates a dark area on the detector imaging surface. Since, in practice, the scattering optics does not function completely ideally, but a small amount of scattered or refracted optical radiation may reach the detector, particles are not totally black in the image.

Furthermore, optical components that are economical to use in practical solutions always scatter a small amount of optical radiation themselves.

If the amount of optical radiation in the image to be formed is such that no pixel is charged up to its maximum charging, even though optical radiation would travel freely through the measurement cell onto the pixel matrix of the detector, the intensities of the optical radiation detected by the pixels can be compared to one another in the same image and in successive images. In that case, the value of at least one pixel of the pixel set related to the object is between a predetermined upper limit and lower limit. The pixel set related to the object generally comprises at least one pixel.

If the optical radiation source 100 and the detector 104 are not on the opposite sides of the measurement cell 102 but at an angle of 90° with respect to each other, for example, the image corresponds to a view where there is at least one light particle on a dark background. Also in this case, the image processing is similar to that in the case where the optical radiation source and the detector are located on the opposite sides of the measurement cell.

Each pixel of the detector 104 converts the intensity of optical radiation that hits it into an electric signal. The electric signals produced are converted into a digital image data signal, which is fed into an automatic image processing unit 106.

The image processing unit 106 may measure the value representing the particle dimension by means of a value related to the particle and proportional to the intensity of the optical radiation detected by at least one pixel. In one embodiment, it is sufficient that the image has been processed into a pixel matrix at some point. The image can be formed directly on a matrix detector comprising pixels, as shown in FIG. 1, or the formed image (for example a photograph on a paper) can be scanned into a pixel matrix.

On comparing the sizes of two particles with each other, the intensity of the optical radiation detected by the pixels can be directly utilised in computing particle dimensions. In that case, the image taken from the measurement cell may correspond to a view where there are bright particles (the value of the pixel related to the particle is high) on a dark background (the value of the pixel related to the background is small) or where there are dark particles (the value related to the particle small) on a light background (the value of the pixel related to the background small). The pixel values in an image comprising at least one particle can be formed, for example, by forming an image from mere medium on the matrix detector 104 by means of the radiation exiting from the measurement cell before or after the formation of the image comprising at least one particle. In the image processing unit 106, a value formed by subtracting each pixel value of the image comprising at least one particle from at least one value of the background image comprising mere medium is set for each pixel of the image comprising at least one particle.

This operation can be performed, for example, by subtracting the value of a pixel of the image comprising at least one particle from the value of each pixel of the background image as follows, for instance $$p_h(l,j) = p_r(l,j) - p_h(l,j),$$

where l is the index of a pixel in one direction of the image, j is the index of a pixel orthogonal to index l, $p_h(l,j)$ is the pixel of an image comprising at least one particle, $p_r(l,j)$ is the pixel of a background image.

The operation can also be performed by subtracting the value of a pixel of the image comprising at least one particle from the average value of the background image as follows, for instance $$p_h(l,j)=p_{t,k}-p_h(l,j),$$

where $p_{t,k}$ is the average value of the background image pixels.

Furthermore, the operation can be performed, for example, by subtracting the value of a pixel of the image comprising at least one particle from the highest value of the background image as follows, for instance $$p_h(l,j)=p_{t,m}-p_h(l,j),$$

where $p_{t,m}$ is the highest value of the background image pixels. After this, the pixel values of the image thus formed in the image processing unit 106 may be divided by at least one value of the image comprising medium as follows $$p_h(l,j)=p_h(l,j)/p_t(l,j).$$

The divisor may also be the average value $p_{t,m}$ of the background image or the highest value $p_{h,m}$ of the image comprising a particle. In that case, the values of the pixels of the image comprising at least one particle are between zero and one (as in FIG. 2). This method is applicable when it is known that in the imagining of a particle sample in a measurement chamber, the image will include at least one particle, which, when imaged on the detector pixel matrix, will totally cover at least one pixel. In that case, the pixel to be covered totally will receive value one. The pixels not totally covered by the particle or particles receive values below one dependent on how large a part of the pixel is covered. The measurement can be performed accurately when the value of at least one pixel of the pixel set related to the object to be measured is within a predetermined upper limit (for example 1) and lower limit (for example 0), without receiving the exact value of the upper or lower limit. The pixel set related to the object generally comprises at least one pixel.

A similar distribution of pixel values is achieved when the measurement employs at least one particle which is imaged so that it totally covers at least one pixel and at least one pixel related to each particle is distinguished from at least one pixel related to the medium by proportioning the values proportional to the intensity of the optical radiation detected by the pixels between zero and one. In that case, the value of at least one pixel related to the medium may be set to a positive number smaller than one. Similarly, value one can be set for at least one pixel that has detected optical radiation whose intensity corresponds to the intensity of the optical radiation detected by at least one pixel totally covered by the particle.

Instead of particles, any imaginable objects may be imaged in a medium or without a medium. In the solution described, a background image may be taken without the object to be examined. The image may be taken of mere medium without particles. Thus the maximal signal value that can be achieved by the imaging arrangement can be determined for each pixel. When this background image is compared with an image comprising at least one object one pixel at a time, the intensity of the optical radiation originally directed at the pixel and refracted or scattered from or absorbed into the object can be determined pixel-specifically as a proportional number. This proportional decrease in the optical radiation intensity can be used to express how large a part of the area of each pixel is covered by the object.

If, for example, the intensity of the optical radiation detected by a certain pixel is 100 in an image taken from the sample and 150 in the background image, it can be assumed that $(150-100)/150=1/3$ of the area is covered by an object on the optical path corresponding to the pixel. To determine the diameter of the object in a desired direction, the ratios in this direction may be added up, and the sum may be multiplied by the diameter of the image area corresponding to one pixel in the corresponding direction. The sum is calculated from adjacent pixels whose ratios include at least one ratio exceeding the set threshold value. In the solution, it is unnecessary to know where the edges of the object are in reality.

Figure 2:
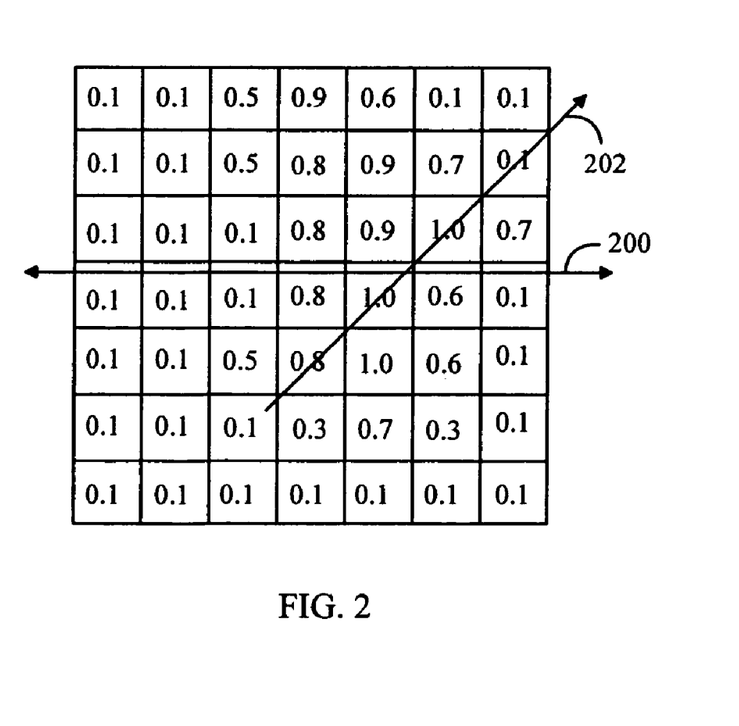
FIG. 2 illustrates a pixel matrix on which an object and background has been imaged.

Now the present solution will be described by means of FIG. 2, which illustrates a pixel matrix and where the value proportional to the intensity of the optical radiation detected by the pixel is marked inside each pixel. At least one pixel related to each particle (FIG. 2 shows only one particle) can be distinguished from at least one pixel related to the medium by means of the intensity of the optical radiation detected by the pixels. In FIG. 2, the value of the pixels of the background formed from the medium is 0.1. A threshold value may be determined for distinction, whereby the pixel values exceeding the threshold value are related to the particle and the values below the threshold value to the medium. Pixels having the threshold value may be classified as particles or as medium. In FIG. 2, the threshold value may be 0.2. The value of the pixels of the medium forming the background can be set to zero in the image processing unit or this value can be obtained by filtering. In that case, the dimension measurement takes account of or is influenced by the value of at least one pixel related only to the particle. The particle area can be determined by adding up the values of all pixels related to the particle. The area of all particles can be determined by adding up the values of all pixels corresponding to the particle in the image. In the case of FIG. 2, the area of the sole particle in the image is $0.5+0.9+0.6+0.5+0.8+0.9+0.8+0.9+1.0+0.7+0.8+1.0+0.6+0.5+0.8+1.0+0.6+0.3+0.7+0.3=14.9$ proportional pixel area units.

Next, the transverse dimension of the particle is measured in direction 200. Pixel values 0.8, 1.0 and 0.6 are added up, which yields $0.8+1.0+0.6=2.4$, i.e. the transverse dimension of the particle is 2.4 proportional pixel width units. The measurements are thus sub-pixel accurate because the pixel values have not been completely contrasted into black and white, i.e. to pixels receiving only values 0 and 1, but the value of at least one pixel is other than 1 or 0 (in this case the pixel values are 0.6 and 0.8).

Without knowing the pixel size, the results obtained can be used for comparing the dimensions of different objects with one another and arranging them in an order according to their dimensions. The measured particle dimensions may also be restored to their physical measurements by proportioning the value representing the measured dimension by the pixel dimension and optical enlargement according to the measurement. If the pixel width is 1 micrometer, the dimension of the transverse direction of the particle imaged on the pixel matrix will be 2.4 micrometers. If no optical enlargement is used, the transverse physical dimension of the particle is 2.4 micrometers. If the optical enlargement is 2, for example, the transverse dimension of the particle imaged on the pixel matrix has to be divided by two, in which case the physical dimension will be 2.4 micrometers/2=1.2 micrometers.

Next, the particle dimension is measured in direction 202. In this case, the sum of the pixel values is $0.8+1.0+1.0=2.7$. Since the pixels are squares in this example for the sake of simplicity, this measurement has to be multiplied by the square root of number 2, which is approximately 1.41. Thus the dimension will be $2.8 \cdot 1.41 \approx 3.9$ proportional pixel units. The measurement accuracy can be further improved by measuring the dimension of the same object from temporally successive images and by averaging the result as follows, for instance:

$$d_a = (1/N) \cdot \sum_{i=0}^{N} d_i,$$

where $d_a$ is the averaged dimension, N is the number of measurements, I is the index of the measurement time, $d_i$ is the dimension measured at measurement time i.

Figure 3A:
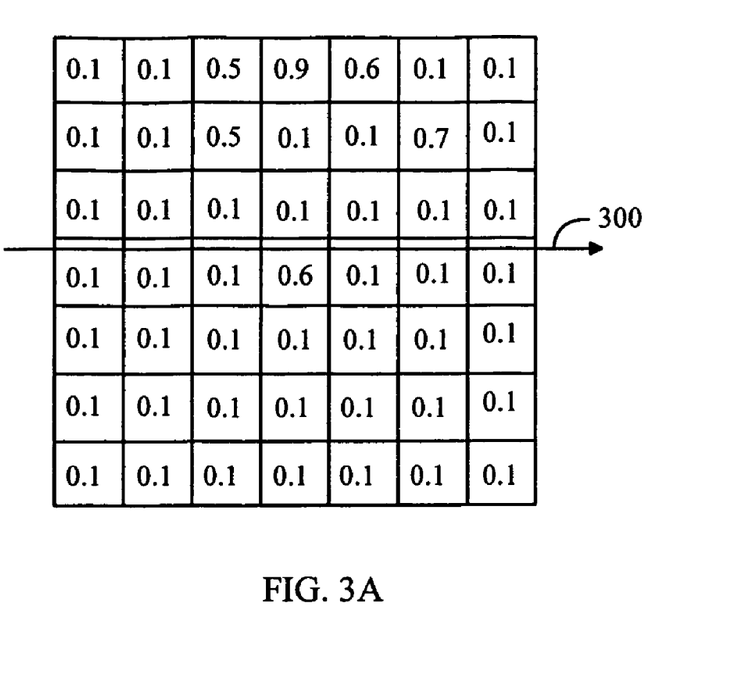
FIGS. 3A to 3C illustrates a moving object and background.
Figure 3B:
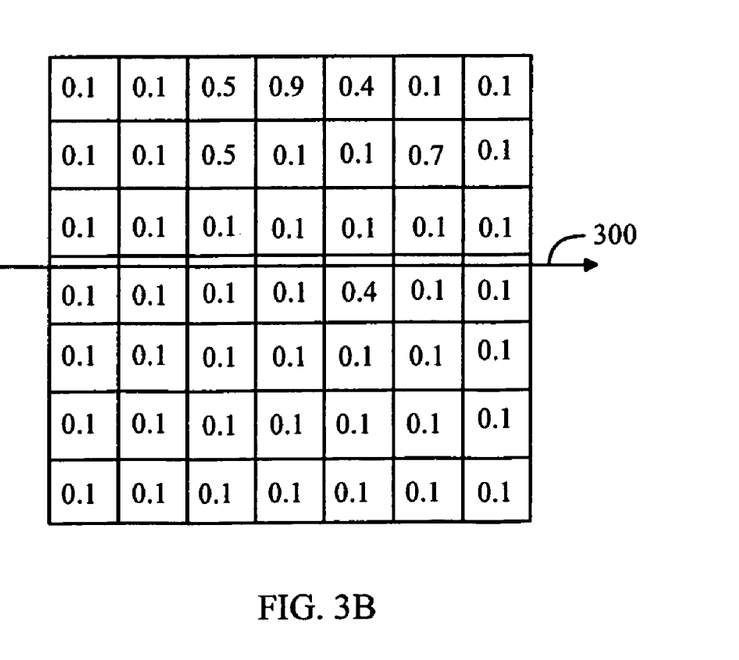
Figure 3C:
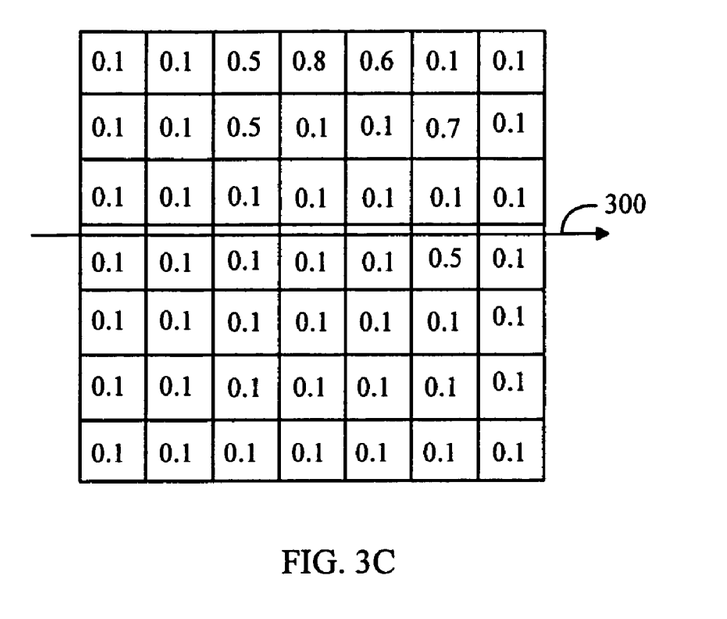

The present solution will be further examined with reference to FIGS. 3A to 3C. The object has moved along path 300 and in FIG. 3A the object is in a pixel whose value is 0.6. In FIG. 3B, the object is in a pixel whose value is 0.4, and in FIG. 3C, the object is in a pixel whose value is 0.5. The images can be formed so that the object is imaged in the same pixel, or images may be processed so that the location of the object does not change in the image. The total sum of the pixels will thus be 1.5. Since one object moves across three pixels, the resulting object dimension will be 1.5/3=0.5. The object is thus clearly smaller than one pixel but its dimension (diameter) can be determined relatively accurately by means of averaging. The pixels where the object is visible need not be successive. If, in temporally successive images, the same pixel is visible in different pixels, which are not necessarily the same or adjacent in the pixel matrix, the object dimension can still be determined using the measurement that averages the pixel values.

The object volume can be estimated by assuming that the depth dimension of the object depends on its width. The object can be assumed to have a desired shape, for example circular or quadrangular. Alternatively, the measurement can be performed in at least two different directions, which allows the width dimension and depth dimension of the object to be measured separately. The volume share of the objects can be formed by dividing the total volume of the objects by the volume of the space imaged from the measurement cell. When the volume of one or more objects in the space defined by the image is also known, the magnitude of the volume share of the objects in the sample can be calculated. When the volume of an object or objects is known, their mass can also be determined by multiplying the volume by the object density. The mass share of the objects can be formed by dividing the total mass of the objects by the above-mentioned volume. The fiber suspension density, for example, can also be determined this way. Thus, according to the solution described, each pixel value is given a physical meaning.

The present solution allows accurate measurement of the object dimensions and a dimension-dependent property even though the image were fuzzy. Fuzziness may be caused by the detector: for example, the object has been imaged on one or on only a few pixels. Even if the object were imaged on a large pixel set, the solution will improve the measurement accuracy. Fuzziness may also result from poor or unsuccessful optical zooming. Furthermore, fuzziness may be caused by optical properties of the medium, such as opacity, etc.

In certain phases of the pulp and paper industry processes, it is usually useful to know the length and width distribution of fibers or of particles larger than fibers (shives) as well as the weight proportion of the fibers (or shives) out of the total solid content of pulp. The width of wood fibers is typically approximately 20 μm and their length varies between 0 and 10 mm. The definition of shives is not very clear, but generally particles with a diameter of at least 75 μm can be classified as shives.

The solution applies well to the determination of the width dimension of objects whose longest diameter (length) is greater than the smallest diameter of one pixel. If the object is so small that its image fits in its entirety within one pixel, only the object diameter or area can be estimated from the image, whereas the length and width cannot be determined separately. In that case, it is impossible to even know whether there is one object or several smaller objects. However, if the number of such objects is large, their total number or volume can be estimated relatively accurately since it may be assumed that any position in a three-dimensional space is equally possible for small objects. This allows the determination of fines consistency in cellulose or paper pulp, for instance.

In the present solution, the refractory indices of the object and the medium (or vacuum) are different. In addition to the particle and medium pairs presented above, the following, for example, may be mentioned: fibers in liquid, where the fibers may be organic (plant fibers, such as wood fibers, or animal fibers) or synthetic (for example glass fiber) and the liquid may be, for example, water; oil drops in water; water drops in oil; gas bubbles in liquid; particles in gas where the particles may be liquid drops or particles of a solid matter. In addition, particles or objects may be measured in a vacuum.

Figure 4:
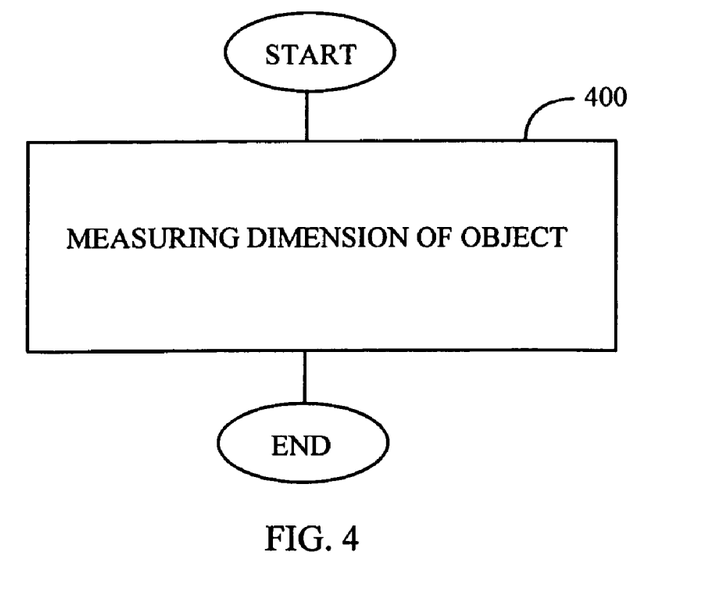
FIG. 4 illustrates a flow chart of a method.

FIG. 4 illustrates a flow chart of the method described. The method comprises forming an image of an object on a matrix detector consisting of pixels. In that case, an object dimension is measured in method step 400 by means of a value related to the object and proportional to the intensity of the optical radiation detected by at least one pixel, the value of at least one of the above-mentioned pixels being between a predetermined upper limit value and lower limit value.

The image processing unit 106 may be implemented as a processor with its software, and the method described is implementable as a computer program. The image processing unit can be alternatively implemented as a hardware structure with separate logical components or one or more application-specific integrated circuits (ASIC). A hybrid of these implementations is also feasible.

The method can be implemented as a computer program product, which is installed in the image processing unit 106 and which encodes a computer process for measuring an object dimension. This computer process is in accordance with the method described. The computer program product can be stored in a computer program distribution medium, which is readable by a computer that implements the program (image processing unit). The distribution medium may be any prior art medium for distributing a computer program from the producer/retailer to the end user. The distribution medium may be, for example, a medium readable by an image processing unit, a program storage medium, a memory readable by an image processing unit, a telecommunications signal assigned to the end user (or image processing unit) by the producer/retailer or a compressed software package.

Even though the invention was described above with reference to the example according to the enclosed drawings, it is clear that the invention is not restricted thereto but it may be modified in various ways within the scope of the appended claims.

That which is claimed:

1. A method of measuring an object from an image of the object, the image comprising a pixel matrix, the method comprising measuring at least one object dimension in parallel with a plane of the image from a single-pixel value proportional to an optical radiation intensity and indicative of the object, for at least one pixel in a selected direction of the pixel matrix of the image, the single-pixel value of the at least one pixel being between a predetermined upper limit value and lower limit value.

2. A method according to claim 1, wherein the object comprises at least one particle dispersed into a medium provided in a measurement cell, a refractive index of the medium differing from a refractive index of the particle, wherein the method further comprises directing optical radiation at the measurement cell; and forming an image of at least one particle in the measurement cell on a matrix detector, the image comprising a plurality of pixels, from the optical radiation exiting from the measurement cell, prior to the measuring step.

3. A method according to claim 2, wherein the forming step further comprises forming an image of a predetermined volume of the medium having the at least one particle dispersed therein from the optical radiation exiting from the measurement cell;

wherein the measuring step further comprises measuring a volume of each particle in the image from the single-pixel value proportional to the optical radiation intensity and indicative of the particle; and wherein the method further comprises measuring the number of particles in the imaged space; and forming the volume share of the particles in the measurement cell by dividing the total volume of the particles by the imaged volume of the medium.

4. A method according to claim 3, further comprising determining the mass of the particles by multiplying the total volume of the particles by the density of the particles; and forming the mass share of the particles by dividing the total mass of the particles by the imaged volume of the medium.

5. A method according to claim 2, further comprising distinguishing at least one pixel related to each particle in the image from at least one pixel related to the medium from the relative intensities of the optical radiation detected for each;

and implementing the single-pixel value of the at least one pixel indicative of the particle in the measuring step.

6. A method according to claim 2, further comprising distinguishing at least one pixel related to each particle in the image from at least one pixel related to the medium from the relative intensities of the optical radiation detected for each;

and setting a value of the at least one pixel related to the medium to number zero in the measuring step.

7. A method according to claim 2, further comprising proportioning the single-pixel value by a pixel dimension in the selected direction.

8. A method according to claim 2, further comprising proportioning the single-pixel value by an optical enlargement.

9. A method according to claim 2, further comprising forming an image of only the medium on the matrix detector, the image consisting of pixels from the optical radiation exiting from the measurement cell;

for each pixel of the image comprising at least one particle, setting a proportioned value by subtracting the intensity value of each pixel of the image comprising at least one particle from an intensity value of a pixel of the image comprising only the medium to form a resulting value; and dividing the resulting value by the intensity value the pixel of the image comprising only the medium.

10. A method according to claim 2, further comprising using, in the measuring step, at least one particle which, when imaged on the matrix consisting of pixels, totally covers at least one pixel; and distinguishing at least one pixel related to each particle from at least one pixel related to the medium by proportioning the single-pixel values proportional to the optical radiation intensity to between zero and one, by setting a positive number smaller than one as the value of at least one pixel related to the medium and setting number one as the value of at least one pixel that has a detected optical radiation intensity corresponding to the optical radiation intensity of a pixel totally covered by the particle.

11. A method according to claim 10, further comprising setting zero as the value of the at least one pixel related to the medium.

12. A computer-readable medium encoded with a computer program capable of being executed within a computer device for measuring an object having an image formed of a pixel matrix, the executed computer program providing a process comprising measuring at least one object dimension in parallel with a plane of the image from a single-pixel value proportional to an optical radiation intensity and indicative of the object, for at least one pixel in a selected direction of the pixel matrix of the image, the single-pixel value of the at least one pixel being between a predetermined upper limit value and lower limit value.

13. A computer-readable medium encoded with a computer program according to claim 12, wherein the object comprises at least one particle dispersed into a medium in a measurement cell, a refractive index of the medium differing from a refractive index of the particle, wherein the measuring step of the process further comprises measuring a particle dimension in parallel with a plane of the image of at least one particle in the measurement cell formed on a matrix detector, the image consisting of pixels, from optical radiation exiting from a measurement cell having the optical radiation directed thereat, from a single-pixel value proportional to the optical radiation intensity and indicative of the particle, for at least one pixel in a selected direction of the pixel matrix of the image, the single-pixel value of the at least one pixel being between a predetermined upper limit value and lower limit value.

14. A computer-readable medium encoded with a computer program according to claim 13, wherein the process further comprises forming an image of a predetermined volume of the medium having the at least one particle dispersed therein from the optical radiation exiting from the measurement cell, wherein the measuring step of the process further comprises measuring a volume of each particle in the image from the single-pixel value proportional to the optical radiation intensity and indicative of the particle; and wherein the process further comprises measuring the number of particles in the imaged space; and forming the volume share of the particles in the measurement cell by dividing the total volume of the particles by the imaged volume of the medium.

15. A computer-readable medium encoded with a computer program according to claim 14, wherein the process farther comprises determining the mass of the particles by multiplying the total volume of the particles by the density of the particles; and forming the mass share of the particles by dividing the total mass of the particles by the imaged volume of the medium.

16. A computer-readable medium encoded with a computer program according to claim 14, wherein the process farther comprises distinguishing at least one pixel related to each particle in the image from at least one pixel related to the medium from the relative intensities of the optical radiation detected for each; and implementing the single-pixel value of the at least one pixel indicative of the particle in the measuring step of the process.

17. A computer-readable medium encoded with a computer program according to claim 14, wherein the process farther comprises distinguishing at least one pixel related to each particle in the image from at least one pixel related to the medium from the relative intensities of the optical radiation detected for each; and setting number zero as a value of at least one pixel related to the medium in the measuring step of the process.

18. A computer-readable medium encoded with a computer program according to claim 14, wherein the process farther comprises proportioning the single-pixel value by a pixel dimension in the selected direction.

19. A computer-readable medium encoded with a computer program according to claim 14, wherein the process farther comprises proportioning the single-pixel value by an optical enlargement.

20. A computer-readable medium encoded with a computer program according to claim 14, wherein the process farther comprises forming an image of only the medium on the matrix detector, the image consisting of pixels from the optical radiation exiting from the measurement cell;

for each pixel of the image comprising at least one particle, setting a proportioned value by subtracting the intensity value of each pixel of the image comprising at least one particle from an intensity value of a pixel of the image comprising only the medium to form a resulting value; and dividing the resulting value by the intensity value the pixel of the image comprising only the medium.

21. A computer-readable medium encoded with a computer program according to claim 14, wherein the process farther comprises using, in the measuring step of the process, a particle which, when imaged on the matrix detector consisting of pixels, totally covers at least one pixel; and distinguishing at least one pixel related to each particle from at least one pixel related to the medium by proportioning the single-pixel values proportional to the optical radiation intensity to between zero and one, so that a positive number smaller than one is set as the value of at least one pixel related to the medium and number one is set as the value of at least one pixel which has a detected optical radiation intensity corresponding to the optical radiation intensity of a pixel totally covered by the particle.

22. A computer-readable medium encoded with a computer program according to claim 21, where the process further comprises setting the value of the at least one pixel related to the medium to zero.

23. A measurement device for measuring an object, the measurement device comprising a matrix detector which consists of pixels and on which an image of the object is formed; and an automatic image processing unit, which is arranged to measure at least one object dimension in parallel with a plane of the image from a single-pixel value proportional to an optical radiation intensity and indicative of the object, for at least one pixel in a selected direction of the pixel matrix of the image, the single-pixel value of the at least one pixel being between a predetermined upper limit value and lower limit value.

24. A measurement device according to claim 23, wherein the object comprises at least one particle dispersed into a medium, and the measurement device further comprises a measurement cell for receiving the medium having the at least one particle dispersed therein, a refractive index of the medium differing from a refractive index of the particle, and an optical radiation source for directing optical radiation at the measurement cell;

wherein the detector farther comprises a matrix consisting of detected pixels and on which the optical radiation exiting from the measurement cell forms the image of at least one particle in the measurement cell.

25. A measurement device according to claim 24, wherein the detector is arranged to form an image of a predetermined volume of the medium having the at least one particle dispersed therein from the optical radiation exiting from the measurement cell; and wherein the image processing unit is arranged to measure a volume of each particle in the image from the single-pixel value proportional to the optical radiation intensity and indicative of the particle;

the image processing unit is arranged to measure the number of particles in the imaged space; and the image processing unit is arranged to form the volume share of the particles in the measurement cell by dividing the total volume of the particles by the imaged volume of the medium.

26. A measurement device according to claim 25, wherein the image processing device is arranged to multiply the total volume of the particles by the density of the particles to form the mass of the particles; and the image processing unit is arranged to form the mass share of the particles by dividing the total mass of the particles by the imaged volume of the medium.

27. A measurement device according to claim 24, wherein the image processing device is arranged to distinguish at least one pixel related to each particle in the image from at least one pixel related to the medium from the relative intensities of the optical radiation detected for each; and the image processing unit is arranged to implement the single-pixel value of the at least one pixel indicative of the particle.

28. A measurement device according to claim 24, wherein the image processing unit is arranged to distinguish at least one pixel related to each particle in the image from at least one pixel related to the medium from the relative intensities of the optical radiation detected for each; and the image processing device is arranged to set number zero as the value of at least one pixel related to the medium.

29. A measurement device according to claim 24, wherein the image processing unit is arranged to proportion the single-pixel value by a pixel dimension in the selected direction.

30. A measurement device according to claim 24, wherein the image processing device is arranged to proportion the single-pixel value by an optical enlargement.

31. A measurement device according to claim 24, wherein the image processing device is arranged to form an image of only the medium on the matrix detector, the image consisting of pixels from the optical radiation exiting from the measurement cell;

the image processing unit is arranged, for each pixel of the image comprising at least one particle, to set a proportioned value by subtracting the intensity value of each pixel of the image comprising at least one particle from an intensity value of a pixel of the image comprising only the medium to form a resulting value; and the image processing unit is arranged to divide the resulting value by the intensity value of the pixel with the highest absolute value.

32. A measurement device according to claim 24, wherein the image processing unit uses a particle which, when imaged on the matrix detector consisting of pixels, totally covers at least one pixel, and the image processing unit is arranged to distinguish at least one pixel related to each particle from at least one pixel related to the medium by proportioning the single-pixel values proportional to the optical radiation intensity to between zero and one, so that a positive number smaller than one is set as the value of at least one pixel related to the medium and number one is set as the value of at least one pixel which has a detected optical radiation intensity corresponding to the optical radiation intensity of a pixel totally covered by the particle.

33. A measurement device according to claim 32, wherein the image processing unit is arranged to set zero as the value of the at least one pixel related to the medium.

34. A measurement device for measuring an object, the measurement device comprising detection means which consists of pixels and on which an image of the object is formed; and automatic image processing means, which are arranged to measure at least one object dimension in parallel with a plane of the image from a single-pixel value proportional to an optical radiation intensity and indicative of the object, for at least one pixel in a selected direction of the pixel matrix of the image, the single-pixel value of the at least one pixel being between a predetermined upper limit value and lower limit value.

35. A measurement device according to claim 34, wherein the object comprises at least one particle dispersed into a medium, and the measurement device further comprises a measurement cell for receiving the medium having the at least one particle dispersed therein, a refractive index of the medium differing from a refractive index of the particle; and means for directing optical radiation at the measurement cell:

wherein the detection means farther comprise a matrix which consists of detected pixels and on which the optical radiation exiting the measurement cell forms the image of at least one particle in the measurement cell.

* * * * *

UNITED STATES PATENT AND TRADEMARK OFFICE
CERTIFICATE OF CORRECTION

PATENT NO. : 7,508,509 B2  Page 1 of 1
APPLICATION NO. : 11/118579
DATED : March 24, 2009
INVENTOR(S) : Lehtikoski et al.

It is certified that error appears in the above-identified patent and that said Letters Patent is hereby corrected as shown below:

Column 10,
Line 62, "farther" should read --further--.

Column 11,
Lines 3, 12, 20, 24, 28 and 41, "farther" should read --further--.

Column 12,
Line 12, "farther" should read --further--.

Column 14,
Line 20, "farther" should read --further--.

Signed and Sealed this

Thirtieth Day of June, 2009

JOHN DOLL
*Acting Director of the United States Patent and Trademark Office*